(12) United States Patent
Li et al.

(10) Patent No.: US 11,865,259 B1
(45) Date of Patent: Jan. 9, 2024

(54) DEVICE AND METHOD FOR RESPIRATORY THERAPY

(71) Applicant: Telesair, Inc., Irvine, CA (US)

(72) Inventors: Bo Li, San Diego, CA (US); Yong Liu, Westminister, CA (US)

(73) Assignee: Telesair, Inc., Irvine, CA (US)

( * ) Notice: Subject to any disclaimer, the term of this patent is extended or adjusted under 35 U.S.C. 154(b) by 0 days.

(21) Appl. No.: 18/147,215

(22) Filed: Dec. 28, 2022

(51) Int. Cl.
*A61M 16/00* (2006.01)
*A61M 16/16* (2006.01)
(Continued)

(52) U.S. Cl.
CPC ......... *A61M 16/024* (2017.08); *A61B 5/0833* (2013.01); *A61B 5/4836* (2013.01); *A61M 16/0057* (2013.01); *A61M 16/109* (2014.02); *A61M 16/16* (2013.01); *G16H 20/40* (2018.01); *G16H 50/30* (2018.01); *A61M 16/0672* (2014.02); *A61M 2016/0027* (2013.01);
(Continued)

(58) Field of Classification Search
CPC .............. A61M 16/00; A61M 16/0057; A61M 16/024; A61M 16/04; A61M 16/06; A61M 16/0672; A61M 16/1075; A61M 16/109; A61M 16/16; A61M 16/161; A61M 2016/0027; A61M 2016/0039; A61M 2205/3331; A61M 2205/3368; A61M 2205/502; A61M 2230/205; A61M 2230/42; A61B 5/0833; A61B 5/4836; G16H 20/40; G16H 50/30
See application file for complete search history.

(56) References Cited

U.S. PATENT DOCUMENTS

2008/0295839 A1* 12/2008 Habashi ............ A61M 16/0051
128/204.22
2011/0120462 A1* 5/2011 Tatkov .............. A61M 16/0012
128/203.14
(Continued)

FOREIGN PATENT DOCUMENTS

WO   WO-2017095241 A2 * 6/2017   ........ A61M 16/0003
WO   WO-2022009000 A1 * 1/2022
(Continued)

OTHER PUBLICATIONS

Roca, Oriol, et al. "An index combining respiratory rate and oxygenation to predict outcome of nasal high-flow therapy." American journal of respiratory and critical care medicine 199.11 (2019): 1368-1376.*

(Continued)

*Primary Examiner* — Joseph D. Boecker
(74) *Attorney, Agent, or Firm* — Maier & Maier, PLLC

(57) ABSTRACT

A device and a method for respiratory therapy. The device is configured with at least two operating modes, which include a first operating mode for providing HFNC support for a patient and a second operating mode for providing NIV support or INV support for the patient; the device includes a memory stored with instructions and a processor, the processor is configured to call and run the instructions stored in the memory to execute operations of: obtaining an ROX index based on first parameters; and triggering mode switching of the device according to the ROX index and a preset triggering strategy for switching the operating mode of the device.

20 Claims, 8 Drawing Sheets

(51) Int. Cl.
    *A61B 5/00*         (2006.01)
    *G16H 50/30*      (2018.01)
    *A61M 16/10*     (2006.01)
    *G16H 20/40*      (2018.01)
    *A61B 5/083*     (2006.01)
    *A61M 16/06*     (2006.01)

(52) U.S. Cl.
    CPC .............. *A61M 2016/0039* (2013.01); *A61M 2016/1025* (2013.01); *A61M 2205/3331* (2013.01); *A61M 2205/3368* (2013.01); *A61M 2205/502* (2013.01); *A61M 2230/205* (2013.01); *A61M 2230/42* (2013.01)

(56) References Cited

U.S. PATENT DOCUMENTS

2019/0262560 A1*   8/2019   Liu ........................ G08B 3/10
2022/0105288 A1     4/2022   Beck et al.
2022/0293262 A1     9/2022   Beck et al.

FOREIGN PATENT DOCUMENTS

WO     WO-2022105586 A1 *   5/2022
WO        2022234496 A1     11/2022

OTHER PUBLICATIONS

Machine translation of WO-2022105586-A1.*
Search Report dated May 17, 2023, in corresponding International Application No. PCT/US23/61818, 10 pages.

* cited by examiner

DEVICE AND METHOD FOR RESPIRATORY THERAPY

TECHNICAL FIELD

The present disclosure relates to the technical field of medical devices for respiratory therapy and, in particular, to an integrated device for respiratory therapy and a method for respiratory therapy based on the respiratory rate-oxygenation (ROX for short) index.

BACKGROUND

High-flow nasal cannula (HFNC) oxygen therapy is a noninvasive and better-compliant treatment for a patient with a respiratory disease caused by the COVID-19 virus. However, when HFNC's respiratory support to a patient is insufficient, escalation to noninvasive ventilation (NIV for short) or invasive ventilation (INV) may be necessary.

This background information is provided to reveal information believed by the applicant to be of possible relevance to the present disclosure. No admission is necessarily intended, nor should be construed, that any of the preceding information constitutes prior art against the present disclosure.

SUMMARY

The disclosure provides a device and method for respiratory therapy, according to the device and the method, three different ventilation modes, including HFNC, NIV, and INV, are enabled on a single integrated device, and the time to change ventilators compared with the prior art is saved, so as to provide timely treatment for patients.

In a first aspect, an embodiment of the present disclosure provides a device for respiratory therapy, where the device is configured with at least two operating modes, and the at least two operating modes include a first operating mode for providing HFNC support for a patient and a second operating mode for providing NIV support or INV support for the patient;

the device includes a memory stored with instructions and a processor, the processor is configured to call and run the instructions stored in the memory to execute operations of:

obtaining an ROX index based on first parameters; and triggering mode switching of the device according to the ROX index and a preset triggering strategy for switching the operating mode of the device.

In a second aspect, an embodiment of the present disclosure provides a method for respiratory therapy, where the method is applied in a device configured with at least two operating modes, and the at least two operating modes include a first operating mode for providing HFNC support for a patient and a second operating mode for providing NIV support or INV support for the patient; where the method includes:

obtaining an ROX index based on first parameters; and triggering mode switching of the device according to the ROX index and a preset triggering strategy for switching the operating mode of the device.

In a third aspect, an embodiment of the present disclosure provides a non-transitory computer-readable storage medium, storing therein computer-executable instructions which, when being executed by a processor, implement the method for respiratory therapy according to the first aspect.

It should be understood that the content described in this section is not intended to identify the key or important features of the embodiments of the present disclosure, nor to limit the scope of the present disclosure. Other features of the present disclosure will be easily understood through the following description.

BRIEF DESCRIPTION OF THE DRAWINGS

The drawings are used for a better understanding of the present solution but do not constitute any limitation on the present disclosure.

DETAILED DESCRIPTION OF THE EMBODIMENTS

Figure 1:
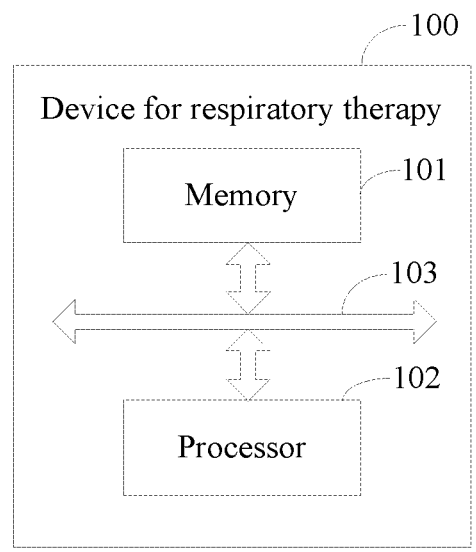
FIG. 1 is a first schematic block diagram of a device for respiratory therapy provided according to an embodiment of the present disclosure.

In the following description, reference is made to the accompanying figures, which form part of the disclosure, and which show, by way of illustration, specific aspects of embodiments of the present disclosure or specific aspects in which embodiments of the present disclosure may be used. It is understood that embodiments of the present disclosure may be used in other aspects and include structural or logical changes not depicted in the figures. The following detailed description, therefore, is not to be taken in a limiting sense, and the scope of the present disclosure is defined by the appended claims.

The term "include" used herein and its variations are open inclusion, that is, "include but not limited to". The term "based on" means "at least partly based on". The term "an embodiment" represents "at least one embodiment"; the term "another embodiment" represents "at least one another embodiment"; and the term "some embodiments" represents "at least some embodiments". Related definitions of other terms will be provided in the following.

It should be noted that concepts such as "first", and "second" mentioned in the present disclosure are merely used to distinguish different apparatuses, modules, or units, but not to limit the sequence or interdependency of functions executed by these apparatuses, modules, or units.

It should be noted that the singular or plural modification mentioned in the present disclosure is illustrative and not restrictive, and those skilled in the art should understand that it should be understood as "one or more" unless clearly defined in the context otherwise.

In recent years, HFNC has been widely used for providing respiratory support for patients who suffer from a respiratory disease caused by the COVID-19 virus and have trouble ensuring enough ventilation by their own respiratory efforts. HFNC can deliver a continuous high flow of heated and humidified gas to a patient through a tube placed in the nostrils. Compared to NIV and INV, HFNC is simpler to use, has better patient compliance, and shows to be a good alternative treatment for hypoxemic acute respiratory failure (ARF for short).

However, when HFNC's respiratory support to a patient is insufficient, the treatment may be needed to escalate to NIV or INV. For example, when the condition of the patient worsens, HFNC may not be applicable and needs to be replaced with NIV or INV. Clinical studies show that the ROX index is a good predictor of HFNC failure in patients with ARF. When the ROX index is lower than a certain value (for example, 4.88), patients may be at high risk of HFNC failure. Therefore, the ROX index can be served as a reference for switching ventilation mode. However, in existing art, HFNC, NIV, and INV are provided in separate ventilators, which results in difficult switching between the three ventilation modes, leading to delayed treatment of patients.

In addition, conventional NIV or INV ventilators may be used with an external humidifier that typically only has a heating function, but not a gas flow rate detecting function. The external humidifier typically has several heating gears, which are shifted by a user according to his own judgment. This imprecise adjustment may lead to many problems, for example, if the heating temperature is too high, the water evaporation may be excessive, which results in forming condensate on the trachea of a patient after the patient inhales the heated and humidified gas, thereby causing infection to the patient.

In view of the above problem, the present disclosure provides an ROX index-based integrated respiratory therapy device and a method for respiratory therapy. According to the device, the three modes, i.e., HFNC, NIV, and INV are integrated into one device and the switching of the modes can be done by the device automatically or with the help of a user (i.e., a doctor). Further, in order to address the above humidification problem, the device can also be provided with humidification components that could be shared among the three modes.

In the following, the technical solutions of the present disclosure will be described in detail with reference to the accompanying drawings.

FIG. 1 shows a first schematic block diagram of a device for respiratory therapy provided according to an embodiment of the present disclosure.

As shown in FIG. 1, a device 100 for respiratory therapy includes a memory 101 stored with instructions and a processor 102.

In a possible implementation, the memory can exchange data with the processor via a bus 103 connected with them. The device 100 is configured with at least two operating modes, and the at least two operating modes include a first operating mode for providing HFNC support for a patient and a second operating mode for providing NIV support or INV support for the patient.

The processor is configured to call and run the instructions stored in the memory to execute operations of:
  obtaining an ROX index based on first parameters; and
  triggering mode switching of the device according to the ROX index and a preset triggering strategy for switching the operating mode of the device.

Specifically, the ROX index is defined as a ratio of pulse oximetry/fraction of inspired oxygen to respiratory rate, i.e., SpO2/FiO2/RR (where "/" represents a division sign), where SpO2 is a blood oxygen saturation level, FiO2 is fraction of inspired oxygen, and RR is a respiratory rate. Therefore, the first parameters for obtaining the ROX index include SpO2, FiO2, and RR. In a possible implementation, the device 100 can obtain the first parameters from different sensors.

After obtaining the ROX index based on the first parameters, the device 100 can trigger mode switching according to the ROX index and the preset triggering strategy for switching the operating mode of the device. In a possible implementation, the preset triggering strategy may be any one of the following a manual-based triggering strategy, a semi-automatic triggering strategy, or a fully automatic triggering strategy. The manual-based triggering strategy may be a strategy that whether conducting the mode switching is determined by the user and the basis (e.g., a comparison result between an ROX value and a threshold) for making the such determination is calculated by the device. The semi-automatic triggering strategy may be a strategy that whether conducting the mode switching is determined by the device but may be confirmed by the user. The fully automatic triggering strategy may be a strategy that whether conducting the mode switching is determined by the device without the confirmation of the user.

With the device for respiratory therapy, three different ventilation modes, including HFNC, NIV, and INV, are enabled on a single integrated device, and the time to change ventilators compared with the prior art is saved, so as to provide timely treatment for patients.

Figure 2:
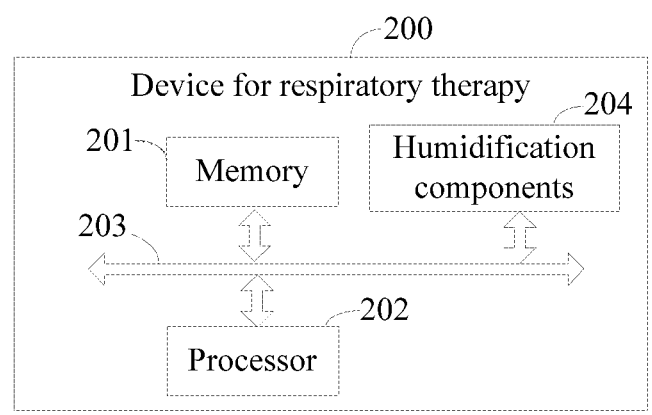
FIG. 2 is a second schematic block diagram of another device for respiratory therapy provided according to an embodiment of the present disclosure.

FIG. 2 is a second schematic block diagram of another device for respiratory therapy provided according to an embodiment of the present disclosure.

In this embodiment, in addition to a memory 201 and a processor 202 that have functions as same as those of memory 101 and processor 102 mentioned above, a device 200 for respiratory therapy may be further provided with humidification components 204 configured for humidifying a gas flow delivered to the patient. With reference to FIG. 2, the humidification components 204 can enable data exchange with the memory 201 and the processor 202 via a bus 203. Data from humidification components 204 can be stored in the memory 201, and the processor 202 can read the data from the memory 201 and control the humidification components 204 to adjust parameters related to a humidification function (e.g., a humidity level of the humidified gas).

Humidifying the gas flow delivered to the patient can reduce the irritation of the gas flow to the nasal passage, therefore most ventilators are used with a humidifier. As mentioned above, a conventional NIV or INV ventilator has to be used with an external humidifier, which may cause many problems. According to the device for respiratory therapy provided in this embodiment, NIV and INV are integrated into a single device and thus share the same humidification components of the single device and can be uniformly controlled by a processor, thereby high-accuracy humidification control can be achieved.

Figure 3:
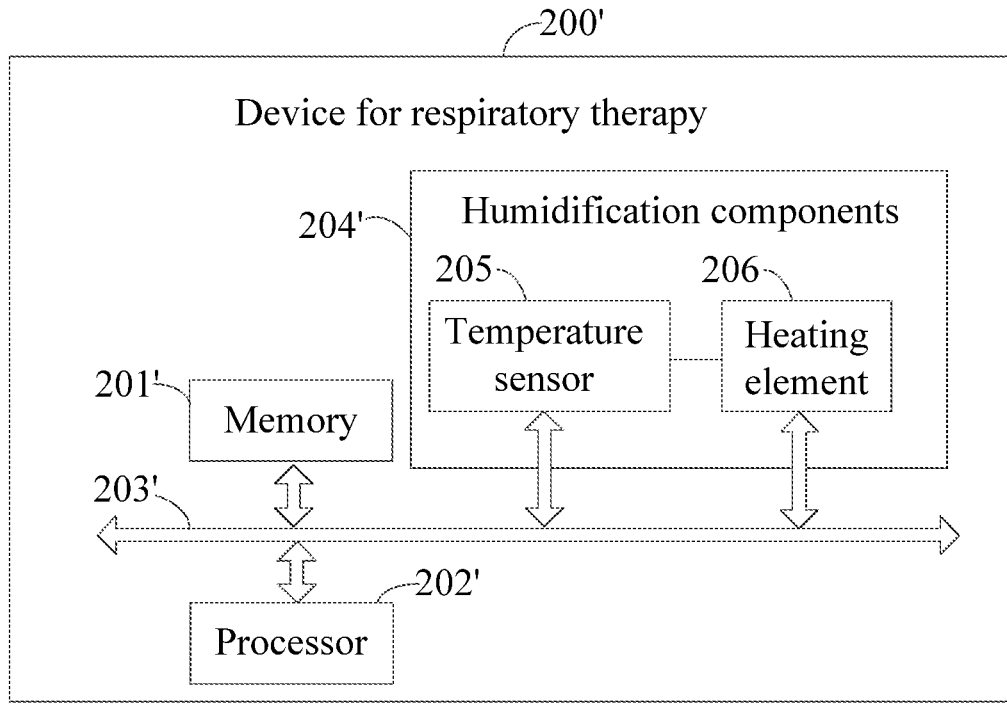
FIG. 3 is a third schematic block diagram of a further device for respiratory therapy provided according to an embodiment of the present disclosure.

FIG. 3 is a third schematic block diagram of a further device for respiratory therapy provided according to an embodiment of the present disclosure. The device 200' for respiratory therapy includes a memory 201', a processor 202', and a bus 203' that have the same functions and connection relationships as the memory 201, the processor 202, and the bus 203 shown in FIG. 2.

In this embodiment, humidification components 204' may further include a temperature sensor 205 and a heating element 206 connected to the temperature sensor 205 compared with the humidification components 204 shown in FIG. 2. The temperature sensor 205 and the heating element 206 are communicatively connected to the processor 202', and the temperature sensor 205 is communicatively connected to the memory 201'. In a possible implementation, the temperature sensor 205 is configured to measure the temperature of the heating element 206 when the device for respiratory therapy is operating in the first operating mode or the second operating mode mentioned above.

The temperature sensor 205 is configured to report the temperature of the heating element 206 to the processor 202', then the processor 202' can adjust the temperature of the heating element 206. In a possible implementation, the temperature of the heating element 206 may have a preset value, and the preset value can be preset stored in the memory 201'. When the temperature of the heating element 206 reaches the preset value, the heated gas flow can reach a desired temperature. If the temperature of the heating element 206 measured by the temperature sensor 205 is higher or lower than the preset value, the processor 202' can adjust the temperature of the heating element 206, until the temperature of the heating element 206 measured by the temperature sensor 205 reaches the preset value, thereby realizing the automatic control of the temperature of the gas flow delivered to the patient.

In a possible implementation, the number of the temperature sensors 205 may be more than one, where one is used to measure the temperature of the heating element 206, and another one is used to measure the temperature of the heated and humidified gas. In a possible implementation, the temperature sensor 205 for measuring the temperature of the heated and humidified gas may be disposed in a respiratory path for guiding the heated and humidified gas to the patient. The temperature sensor 205 can send the temperature data of the heated and humidified gas to the processor 202' mentioned above. The processor 202' mentioned above can be configured to adjust the temperature of the heating element 206 according to the measured temperature of the heating element 206 and the temperature of the heated and humidified gas. Similarly, the temperature of the heated and humidified gas may also have a preset value stored in the memory 201', and the processor 202' can read the preset value of the temperature of the heated and humidified gas from the memory 201' to adjust the temperature of the heating element 206 according to the preset value of the temperature of the heated and humidified gas.

Figure 4:
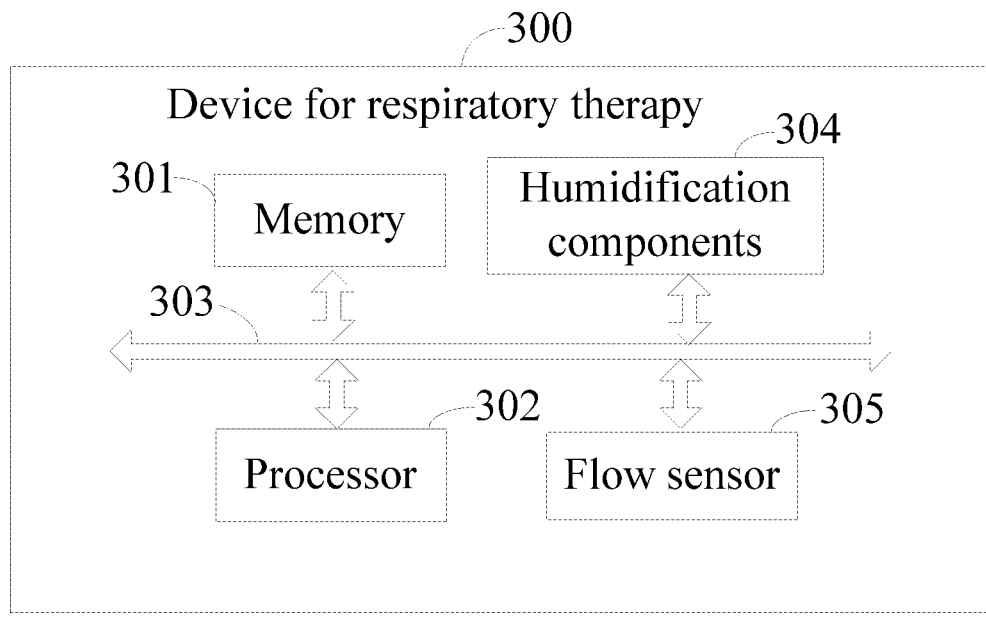
FIG. 4 is a fourth schematic block diagram of yet a further device for respiratory therapy provided according to an embodiment of the present disclosure.

FIG. 4 is a fourth schematic block diagram of yet a further device for respiratory therapy provided according to an embodiment of the present disclosure, in which the memory 301, processor 302, and humidification components 304 respectively have the same functions as the memory 201, processor 202, and humidification components 204 mentioned above. In addition, the humidification components 304 can have the same parts and functions as the humidification components 204'.

In this embodiment, a device 300 for respiratory therapy is provided with a flow sensor 305 configured for measure a flow rate of the gas flow delivered to the patient, where the flow sensor 305 is communicatively connected to the memory 301 and the processor 302 via a bus 303 to enable data exchange with them.

In a possible implementation, the humidity of the gas flow is adjustable by the humidification components 304 based on the flow rate. In a possible implementation, the temperature of the heating element is adjustable based on the flow rate.

For example, in order to achieve the desired humidification output >12 or 33 mg/L (i.e., more than 12 mg or 33 mg of water vapor per liter of the gas) depending on the application for HFNC, NIV, or INV, in the heated and humidified gas flow that is delivered to the patient, the temperature of the heating element for heating up the liquid stored in the chamber needs to be controlled to a certain reference profile. The processor 302 can first roughly adjust the temperature of the heating element to an approximate value by the following formula:

$$T_{heating\ element}(t) = a_n \cdot Q(t)^n + a_{n-1} \cdot Q(t)^{n-1} + a_{n-2} \cdot Q(t)_{n-2} + \ldots + a_1 \cdot Q(t) + a_0$$

where $T_{heating\ element}(t)$ is the temperature of the heating element at time t; $Q(t)$ is the flow rate of the gas going through the chamber at time t, where the flow rate here refers to a flow rate of the gas before heating and humidification; and $a_n$, $a_{n-1}$, $a_{n-2}$, ..., $a_1$, $a_0$ are coefficients of the polynomial equation, where n is a positive integer.

In a possible implementation, the coefficients of the polynomial equation can be obtained by fitting experimental data of a series of experiments and can be pre-stored in the memory. For example, it is possible to test the temperature of the heating element at different gas flow rates when the desired temperature (e.g., the body temperature of 37° C.) of the heated and humidified gas is reached, record values of the gas flow rates and temperature values of the heating element corresponding to the values of the gas flow rates, and obtain the relationship between the gas flow and the temperature of the heating element by fitting the recorded values of the gas flow rates and temperature values of the heating element corresponding to the values of the gas flow rates, thereby obtaining the coefficients of the polynomial equation.

In a possible implementation, in the experiments mentioned above, the flow rate of the gas going through the chamber can be controlled from a minimum flow rate to a maximum flow rate by a certain increment, where the range of gas flow rate may be between 2 LPM (litre per minute) to 80 LPM, and the increment may be 2 LPM. For example, when the gas flow rate measured by the flow sensor 305 reaches 2 LPM, record the temperature of the heating element at the gas flow rate of 2 LPM when the temperature of the gas flow delivered to the patient is maintained at 37° C.; when the gas flow rate measured by the flow sensor 305 reaches 4 LPM (the gas flow rate is increased by 2 LPM), record the temperature of the heating element at the gas flow rate of 4 LPM when the temperature of the gas delivered to the patient is maintained at 37° C., ..., repeat the steps mentioned foregoing until the gas flow rate measured by the flow sensor 305 reaches 80 LPM. Through such experiments, the temperature of the heating element at different gas flow rates when the desired temperature (e.g., the body temperature of 37° C.) of the heated and humidified gas is reached can be obtained, thereby obtaining the coefficients of the polynomial equation.

In a possible implementation, when the gas delivered to the patient needs to be heated and humidified, the processor 302 can read the coefficients stored in the memory 301 and calculate the approximate temperature of the heating element in combination with the gas flow rate according to the formula mentioned above. In a possible implementation, the temperature of the heating element may be within a range of 50° C.~90° C.

In a possible implementation, the humidification components 304 may include a circuit, which may be connected to the humidification components, and can be configured to communicate with the processor 302 and control the operation of the humidification components.

After the above rough adjustment, fine-tuning of the temperature of the heating element may be executed based on the temperature of the heated and humidified gas. For example, after the rough adjustment, if the temperature of the heated and humidified gas has not reached the desired temperature, the processor can further adjust the temperature of the heating element until the measured temperature of the heated and humidified gas reaches the desired temperature. Through the combination of the rough adjustment and fine-tuning of the heating element, the temperature of the heated and humidified gas flow leaves the chamber precisely to the desired temperature.

With the above device for respiratory therapy, mode switching between HFNC and NIV/INV can be achieved according to the ROX index and the preset triggering strategy for switching the operating mode of the device.

As mentioned above, the preset triggering strategy is any one of the following: the manual-based triggering strategy, the semi-automatic triggering strategy, or the fully automatic triggering strategy. The difference between the three strategies is that the degree of the intervention of the user (i.e., physician) in mode switching between the first operating mode and the second operating mode is different, that is, the present disclosure can adjust the control degree of the device on the mode switching as needed.

In an embodiment of the present disclosure, when the preset triggering strategy is the manual-based triggering strategy, the processor is further configured to call and run the instructions stored in the memory to execute operations of:
  determining whether the ROX index is smaller than a preset value;
  upon determining that the ROX index is smaller than the preset value, sending a first notification to a user terminal, where the first notification indicates that the ROX index is smaller than the preset value;
  upon determining that the ROX index is not smaller than the preset value, sending a second notification to the user terminal, where the second notification indicates that the ROX index is not smaller than the preset value;
  triggering the mode switching of the device based on a switching instruction from a user.

In a possible implementation, the preset value of the ROX index mentioned above maybe 4.88. This threshold may be used to identify a patient that may be at high risk of HFNC failure. If the preset value of the ROX index is smaller than the threshold, the HFNC mode (i.e., the first operating mode) may need to be switched to the NIV mode or INV mode (i.e., the second operating mode); and if the preset value of the ROX index is equal to or larger than the threshold, the NIV or INV modes may need to be switched to the HFNC mode.

In this embodiment, upon determining that the ROX index is smaller than the preset value, the processor can send the first notification to the user terminal, where the first notification indicates that the ROX index is smaller than the preset value; upon determining that the ROX index is not smaller than the preset value, the processor can send the second notification to the user terminal, where the second notification indicates that the ROX index is not smaller than the preset value. After receiving the first notification, the user terminal may remind the user (e.g., a physician) that the ROX index is lower than or not lower than the preset value, so that the user can be reminded that the patient may be at high risk of HFNC failure or not, and then the user may determine whether it is necessary to conduct a mode switching based on the first notification or the second notification.

For example, after the user is reminded that the ROX index is smaller than or not smaller than the preset value by the user terminal, the user may trigger the switching instruction by the user terminal to switch the operating mode of the device. In this example, the user has known the current operating mode of the device. If the user is unaware of the current operating mode of the device, the user terminal may also acquire the operating mode of the device based on communication with the device, for example, in a request and response manner, and then the user could know the current operating mode of the device from his user terminal.

For another example, after the user is reminded that the ROX index is smaller than or not smaller than the preset value by the user terminal, the user may visit the patient to learn the actual physical condition of the patient and the operating mode of the device, and determine whether it is necessary to conduct the mode switching further according to the operating mode of the device and the actual physical condition of the patient. If the user determines to switch the operating mode of the device, the user may trigger the switching instruction by the input apparatus on the device, for example, the user may trigger the switching instruction by touching a button on the device to generate the switching instruction, and then the device can perform mode switching based on the generated switching instruction. Alternatively, the user may trigger the switching instruction by the user terminal, for example, the user may trigger the switching instruction by touching a control on the screen of the terminal device or a button on the terminal device, and then the terminal device can generate the switching instruction and send it to the device, the device for respiratory therapy can then switch its operating mode once it receives the switching instruction from the user.

In a possible implementation, when the device is in the first operating mode, the switching instruction indicates to switch from the first operating mode to the second operating mode; when the device is in the second operating mode, the switching instruction indicates to switch from the second operating mode to the first operating mode.

With the device for respiratory therapy in this embodiment, the ROX index that can reflect the physical condition of the patient can be monitored automatically and notified to the user in time for providing the basis for the user to determine whether to conduct the mode switching, so that the user can learn the change of the ROX index without frequently visiting the device, and can further make an appropriate response in time, so that the patient can get timely treatment.

In an embodiment of the present disclosure, when the preset triggering strategy is the semi-automatic triggering strategy, the processor is further configured to call and run the instructions stored in the memory to execute operations of:

determining whether the ROX index is smaller than a preset value;

determining an operating mode of the device;

upon determining that the ROX index is smaller than the preset value and the device is in the first operating mode, sending a third notification to a user terminal, where the third notification indicates to switch from the first operating mode to the second operating mode;

upon determining that the ROX index is not smaller than the preset value and the device is in the second operating mode, sending a fourth notification to the user terminal, where the fourth notification indicates to switch from the second operating mode to the first operating mode;

upon receiving a switch confirming instruction from the user terminal, switching the device from the current operating mode to another different operating mode.

In this embodiment, the device can determine the operating mode of the device and how to switch the operating mode of the device based on the ROX index and the operating mode of the device, to send the third notification or the fourth notification to the user terminal, so that the user (e.g., a physician) of the user terminal can be reminded that it may be necessary to switch from the first operating mode to the second operating mode, or from the second operating mode to the first operating mode. The user may determine whether to conduct the mode switching according to the third notification or the fourth notification and send the switch confirming instruction by the user terminal to the device if he determines that the current operating mode needs to be switched in accordance with the third notification or the fourth notification. Upon receiving the switch confirming instruction from the user terminal, the processor of the device can control the device to switch from the current operating mode to another operating mode.

With the device for respiratory therapy in this embodiment, it is the device that makes the determination of whether to switch the operating mode, the user simply needs to confirm whether to perform the mode switching, which not only enables the patient to get timely treatment but also reduces the burden on a physician.

In an embodiment, when the preset triggering strategy is the fully automatic triggering strategy, the processor is further configured to call and run the instructions stored in the memory to execute the operations of:

determining whether the ROX index is smaller than a preset value;

determining an operating mode of the device;

upon determining that the ROX index is smaller than the preset value and the device is in the first operating mode, triggering the device to switch from the first operating mode to the second operating mode; and upon determining that the ROX index is not smaller than the preset value and the device is in the second operating mode, triggering the device to switch from the second operating mode to the first operating mode.

In this embodiment, the device can determine the operating mode of the device and how to switch the operating mode of the device based on the ROX index and the operating mode of the device, and then the device can automatically switch from the first operating mode to the second operating mode when determining that the ROX index is smaller than the preset value and the device is in the first operating mode, or switch from the second operating mode to the first operating mode when determining that the ROX index is not smaller than the preset value and the device is in the second operating mode.

After triggering mode switching of the device according to any one of the preset triggering strategies described above, the user (i.e., a physician) may need to conduct a subsequent operation. For example, after switching the device from the HFNC mode to the NIV mode, the user may need to help the patient wear a ventilating mask; after switching the device from the HFNC mode to the INV mode, the user may need to insert an endotracheal tube into the patient; after switching the device from the INV mode/NIV mode to the HFNC mode, the user may need to help the patient wear a nasal cannula.

As mentioned above, the ROX index is an important indicator to determine whether to switch the operating mode of the device, and the ROX index is obtained based on the first parameters. In the present disclosure, the device mentioned in the above embodiment can obtain the first parameters, including SpO2, FiO2, and RR, by different sensors.

In a possible implementation, the first parameters are measured by different sensors; the sensors include a first sensor configured for measuring oxygen saturation (i.e., pulse oximetry), a second sensor configured for measuring a fraction of inspired oxygen, and a third sensor configured for measuring a respiratory rate; and the processor is further configured to call and run the instructions stored in the memory to execute operations of:

calculating the ROX index according to the oxygen saturation measured by the first sensor, the fraction of inspired oxygen measured by the second sensor, and the respiratory rate measured by the third sensor.

In a possible implementation, the first sensor is a pulse oximetry, the second sensor is an oxygen concentration sensor, and the third sensor is a flow sensor or a pressure sensor. Oxygen saturation is the oxygen saturation of the gas delivered to the patient. It should be understood that the gas is consisted of oxygen and compressed air to be delivered to the patient for providing respiratory support. Other sensors can be used to measure the first parameters mentioned above, which will not be limited by the present disclosure.

Figure 5:
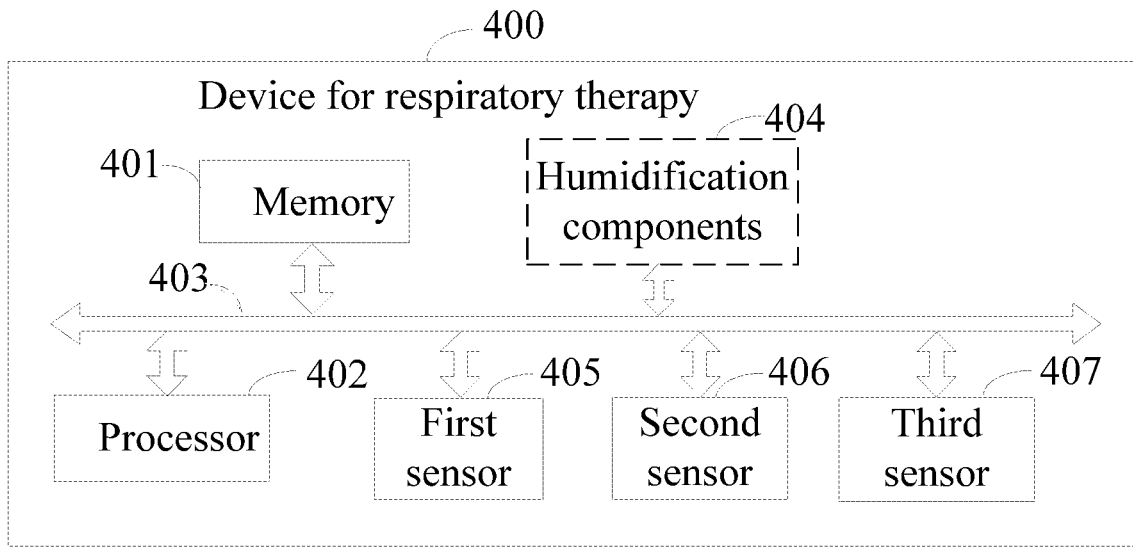
FIG. 5 is a fifth schematic block diagram of yet a further device for respiratory therapy provided according to an embodiment of the present disclosure.

In a possible implementation, the sensors used to obtain the first parameters are integrated into the device and communicatively connected to the device, as shown in FIG. 5, which is a fifth schematic block diagram of yet a further device for respiratory therapy provided according to an embodiment of the present disclosure. The device 400 for respiratory therapy includes a memory 401, a processor 402, a bus 403, a first sensor 405, a second sensor 406 and a third sensor 407. In a possible implementation, the device 400 for respiratory therapy may include humidification components 404 that have the same functions as the humidification components 204, 204', or 304 shown in FIG. 2, FIG. 3 and FIG. 4, respectively. Similarly, the memory 401, the processor 402, and the bus 403 have the same functions as the memory, the processor, and the bus as shown in FIG. 2, FIG. 3 and FIG. 4 respectively. The sensors 405 to 407 can communicatively connected to the processor 402 and the memory 401 via the bus 403 to enable data exchange with them.

In a possible implementation, one or more of the sensors may be an external sensor that is communicatively connected to the device.

In order to obtain the ROX index, in a possible implementation, the processor is further configured to call and run the instructions stored in the memory to execute operations of:
- collecting multiple groups of the first parameters measured in a preset time interval;
- calculating temporary ROX indexes based on the multiple groups of the first parameters respectively;
- averaging the temporary ROX indexes to obtain the ROX index.

In a possible implementation, the time interval can be preset by the user through the input apparatus on the device or through the user terminal. For example, the input apparatus includes a keyboard and pointing apparatus (e.g., a mouse or a trackball). For another example, the user can input the preset time interval on the user terminal, then the user terminal can send a message carrying the preset time interval to the device. As mentioned above, the ROX index can be obtained by averaging the temporary ROX indexes by calculating the temporary ROX indexes based on the collected multiple groups of the first parameters over the preset time interval respectively, through which, the preset time interval can be set flexibly by the user according to the conditions of different patients as required, thus rendering the mode switching more reasonable.

In a possible implementation, the device can be configured with an emergency mechanism for the method of obtaining the ROX index by averaging the temporary ROX indexes. Specifically, when the temporary ROX index is excessively low, the emergency mechanism can be triggered by the device. In a possible implementation, when a temporary ROX index is lower than a second threshold, the emergency mechanism is triggered. In a possible implementation, the emergency mechanism is that: when a temporary ROX index is lower than the second threshold, the device does not trigger mode switching according to the ROX index obtained by averaging the temporary ROX indexes and the preset trigger strategy but triggers mode switching according to the temporary ROX index and the preset triggering strategy. In a possible implementation, the second threshold can be preset by the user. In a possible implementation, when the ROX index is equal to or higher than the second threshold, the emergency mechanism can be cancelled, that is, the device can trigger mode switching according to the ROX index obtained by averaging the temporary ROX indexes and the preset trigger strategy.

Figure 6:
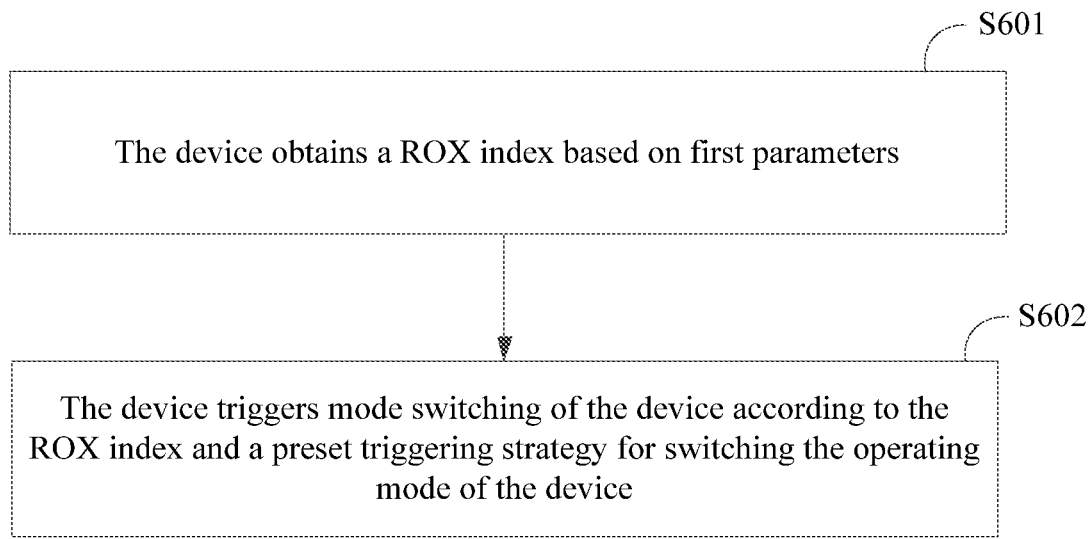
FIG. 6 is a schematic flowchart of a method for respiratory therapy according to an embodiment of the present disclosure.

FIG. 6 is a schematic flowchart of a method for respiratory therapy according to an embodiment of the present disclosure, which may be applied in the device for respiratory therapy provided according to the embodiments of the present disclosure. As mentioned above, the device for respiratory therapy is configured with at least two operating modes, and the at least two operating modes include a first operating mode for providing HFNC support for a patient and a second operating mode for providing NIV support or INV support for the patient. The method includes:
- step S601, the device obtains an ROX index based on first parameters; and
- step S602, the device triggers mode switching of the device according to the ROX index and a preset triggering strategy for switching the operating mode of the device.

As described in the above embodiments, the ROX index is a ratio of pulse oximetry/fraction of inspired oxygen to respiratory rate (i.e., SpO2/FiO2/RR, where "/" represents a division sign), and the first parameters for obtaining the ROX index include SpO2, FiO2, and RR.

In a possible implementation, the first parameters can be obtained from different sensors. In a possible implementation, the different sensors include a first sensor configured for measuring oxygen saturation, a second sensor configured for measuring a fraction of inspired oxygen, and a third sensor configured for measuring a respiratory rate.

In a possible implementation, step S601 of obtaining the ROX index based on the first parameters by the device may include:
- the device calculates the ROX index according to the oxygen saturation measured by the first sensor, the fraction of inspired oxygen measured by the second sensor, and the respiratory rate measured by the third sensor.

In this implementation, the device can obtain the ROX index by calculating the ROX index according to the oxygen saturation measured by the first sensor, the fraction of inspired oxygen measured by the second sensor, and the respiratory rate measured by the third sensor.

In a possible implementation, the first sensor is a pulse oximetry, the second sensor is an oxygen concentration sensor, and the third sensor is a flow sensor or a pressure sensor. It should be understood that other sensors can be used to measure the first parameters mentioned above, which will not be limited by the present disclosure. In a possible implementation, the sensors used to obtain the first parameters are integrated into the device and communicatively connected to the device. In a possible implementation, one or more of the sensors may be an external sensor that is communicatively connected to the device.

Figure 7:
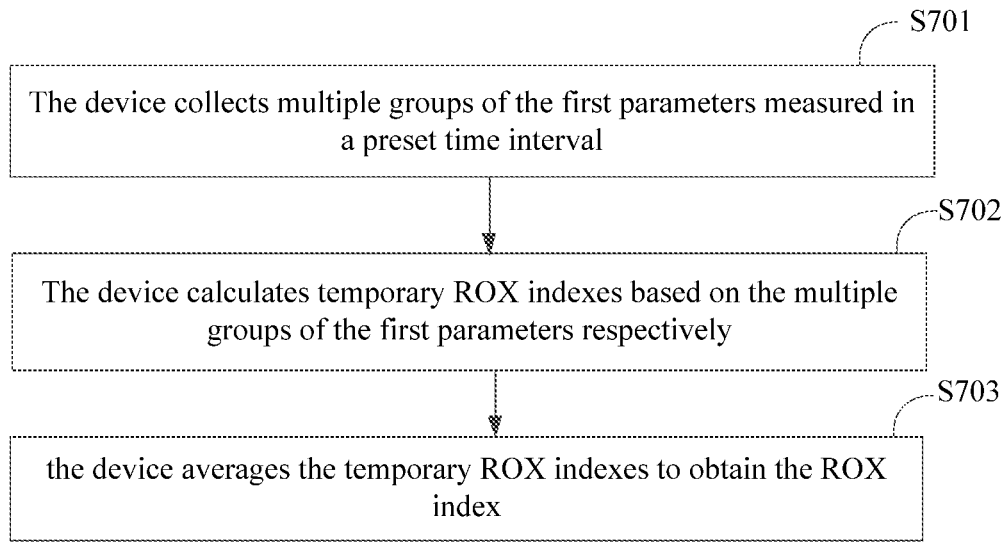
FIG. 7 is a schematic flowchart of a method for obtaining a ROX index based on first parameters.

In a possible implementation, step S601 of obtaining the ROX index based on the first parameters by the device may include the following steps (as shown in FIG. 7):
- step S701, the device collects multiple groups of the first parameters measured in a preset time interval;
- step S702, the device calculates temporary ROX indexes based on the multiple groups of the first parameters respectively;
- step S703, the device averages the temporary ROX indexes to obtain the ROX index.

In this implementation, before calculating the ROX index based on the first parameters, the device can collect the multiple groups of the first parameters measured in the preset time interval. In a possible implementation, the time interval can be preset by the user through the input apparatus on the device or through the user terminal. For example, the input apparatus includes a keyboard and pointing apparatus (e.g., a mouse or a trackball). For another example, the user can input the preset time interval on the user terminal, then the user terminal can send the preset time interval carried in a message to the device.

After collecting the multiple groups of the first parameters, the device can calculate the temporary ROX indexes based on the multiple groups of the first parameters respectively, that is, calculate a temporary ROX index for each of the multiple groups of the first parameters, so as to obtain the temporary ROX indexes corresponding to the multiple groups of the first parameters. By averaging the temporary ROX indexes, the ROX index is obtained. It should be noted that the ROX index obtained by averaging the temporary ROX indexes is an ROX index according to which the device triggers the mode switching of the device.

In a possible implementation, the time interval can be preset by the user through the input apparatus on the device or through the user terminal. For example, the input apparatus includes a keyboard and pointing apparatus (e.g., a mouse or a trackball). For another example, the user can input the preset time interval on the user terminal, then the user terminal can send the preset time interval carried in a message to the device. As mentioned above, the ROX index can be obtained by averaging the temporary ROX indexes by calculating the temporary ROX indexes based on the collected multiple groups of the first parameters over the preset time interval respectively, through which, the preset time interval can be set flexibly by the user according to the conditions of different patients as required, thus rendering the occasion of the mode switching more reasonable.

In a possible implementation, the method for respiratory therapy may include an emergency mechanism for the method of obtaining the ROX index by averaging the temporary ROX indexes. Specifically, when the temporary ROX index is excessively low, the emergency mechanism can be triggered by the device. In a possible implementation, when a temporary ROX index is lower than a second threshold, the emergency mechanism is triggered. In a possible implementation, the emergency mechanism is that: when a temporary ROX index is lower than the second threshold, the device does not trigger mode switching according to the ROX index obtained by averaging the temporary ROX indexes and the preset trigger strategy but triggers mode switching according to the temporary ROX indexes and the preset triggering strategy. In a possible implementation, the second threshold can be preset by the user. In a possible implementation, when the ROX index is equal to or higher than the second threshold, the emergency mechanism can be cancelled, that is, the device can trigger mode switching according to the ROX index obtained by averaging the temporary ROX indexes and the preset trigger strategy.

In a possible implementation, after obtaining the ROX index based on the first parameters according to the methods mentioned above, the mode switching of the device between the first operating mode and the second operating mode can be triggered by the device according to the ROX index and the preset triggering strategy for switching the operating mode of the device. In a possible implementation, the preset triggering strategy may be any one of the following: a manual-based triggering strategy, a semi-automatic triggering strategy, or a fully automatic triggering strategy.

Figure 8:
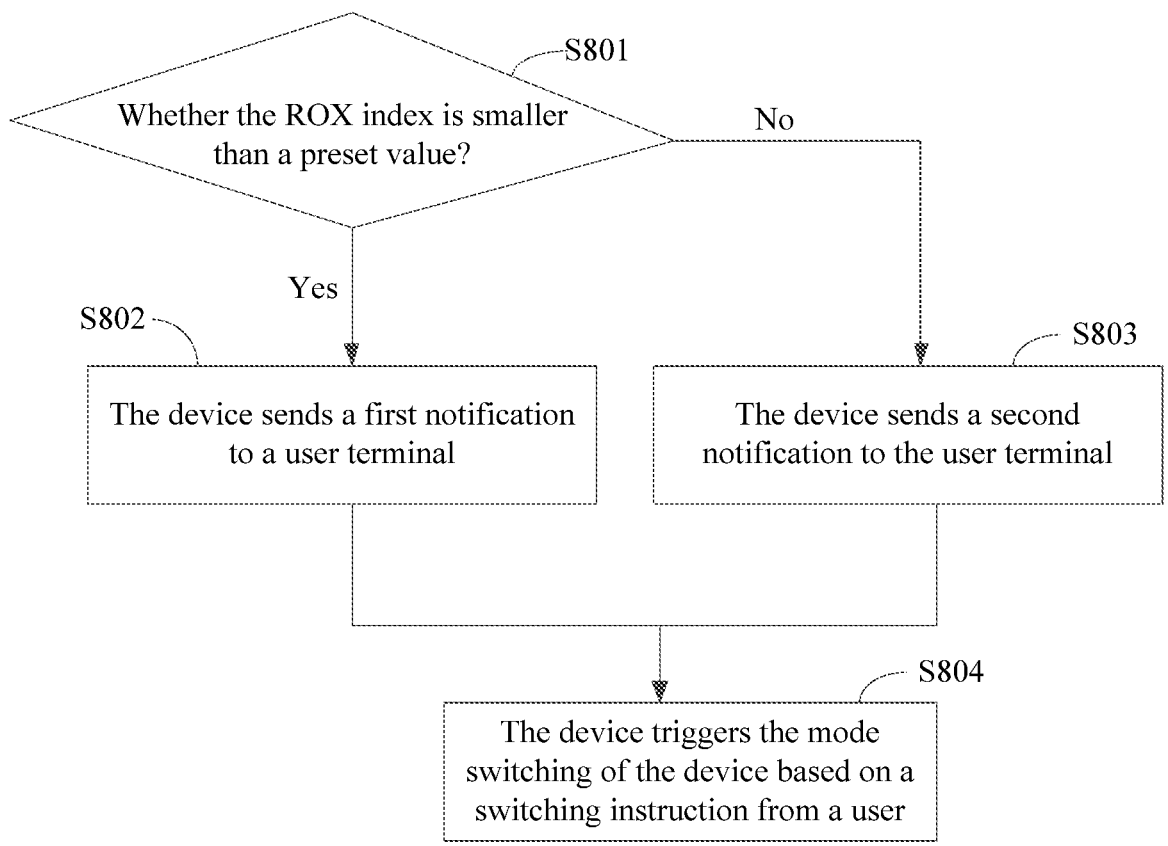
FIG. 8 is a schematic flowchart of a manual-based triggering strategy for triggering mode switching of a device for respiratory therapy.

In a possible implementation, when the preset triggering strategy is the manual-based triggering strategy, step S602 of triggering mode switching of the device according to the ROX index and a preset triggering strategy for switching the operating mode of the device may include the following steps (as shown in FIG. 8):

step S801, the device determines whether the ROX index is smaller than a preset value;
step S802, upon determining that the ROX index is smaller than the preset value, the device sends a first notification to a user terminal, where the first notification indicates that the ROX index is smaller than the preset value;
step S803, upon determining that the ROX index is not smaller than the preset value, the device sends a second notification to the user terminal, where the second notification indicates that the ROX index is not smaller than the preset value;
step S804, the device triggers the mode switching of the device based on a switching instruction from a user.

As described above, the preset value of the ROX index mentioned above maybe 4.88. This threshold may be used to identify a patient that may be at high risk of HFNC failure. In a possible implementation, the threshold may be preset by the user.

In this implementation, a determination is made whether the ROX index is smaller than the preset value. Upon determining that the ROX index is smaller than the preset value, the device sends the first notification to the user terminal to remind the user via the user terminal that the ROX index is smaller than the preset value (that is, a patient may be at high risk of HFNC failure), and then the user may determine whether it is necessary to conduct a mode switching based on the first notification. Upon determining that the ROX index is not smaller than the preset value, the device sends the second notification to the user terminal to remind the user via the user terminal that the ROX index is not smaller than the preset value (that is, a patient may be not at high risk of HFNC failure), and then the user may determine whether it is necessary to conduct a mode switching based on the second notification.

For example, after the user is reminded that the ROX index is smaller than or not smaller than the preset value by the user terminal, the user may trigger the switching instruction by the user terminal to switch the operating mode of the device. In this example, the user has known the current operating mode of the device. If the user is unaware of the current operating mode of the device, the user terminal may also acquire the operating mode of the device based on communication with the device, for example, in a request and response manner, and then the user could know the current operating mode of the device from his user terminal.

For another example, after the user is reminded that the ROX index is smaller than or not smaller than the preset value by the user terminal, the user may visit the patient to learn the actual physical condition of the patient and the operating mode of the device, and determine whether it is necessary to conduct the mode switching further according to the operating mode of the device and the actual physical condition of the patient. If the user determines to switch the operating mode of the device, the user may trigger the switching instruction by the input apparatus on the device, for example, the user may trigger the switching instruction by touching a button on the device to generate the switching instruction, and then the device can perform mode switching based on the generated switching instruction. Alternatively, the user may trigger the switching instruction by the user terminal, for example, the user may trigger the switching instruction by touching a control on the screen of the terminal device or a button on the terminal device, and then the terminal device can generate the switching instruction and send it to the device, the device for respiratory therapy can then switch its operating mode once it receives the switching instruction from the user.

In a possible implementation, when the device is in the first operating mode, the switching instruction indicates to switch from the first operating mode to the second operating mode; when the device is in the second operating mode, the switching instruction indicates to switch from the second operating mode to the first operating mode.

According to the method for respiratory therapy, by obtaining the ROX index based on the first parameters, and triggering mode switching of the device according to the ROX index and the preset triggering strategy for switching the operating mode of the device, the ROX index that can reflect the physical condition of the patient can be monitored automatically and notified to the user in time for providing the basis for the user to determine whether to conduct the mode switching, so that the user can learn the change of the ROX index without frequently visiting the device, and can further make an appropriate response in time, so that the patient can get timely treatment.

In a possible implementation, when the preset triggering strategy is the semi-automatic triggering strategy, step S602 of triggering mode switching of the device according to the ROX index and a preset triggering strategy for switching the operating mode of the device may include the following steps:

S901, the device determines whether the ROX index is smaller than a preset value;

S902, the device determines an operating mode of the device;

S903, upon determining that the ROX index is smaller than the preset value and the device is in the first operating mode, the device sends a third notification to a user terminal, where the third notification indicates to switch from the first operating mode to the second operating mode;

S904, upon determining that the ROX index is not smaller than the preset value and the device is in the second operating mode, the device sends a fourth notification to the user terminal, where the fourth notification indicates to switch from the second operating mode to the first operating mode;

S905, upon receiving a switch confirming instruction from the user terminal, the device switches from the current operating mode to another different operating mode.

Figure 9A:
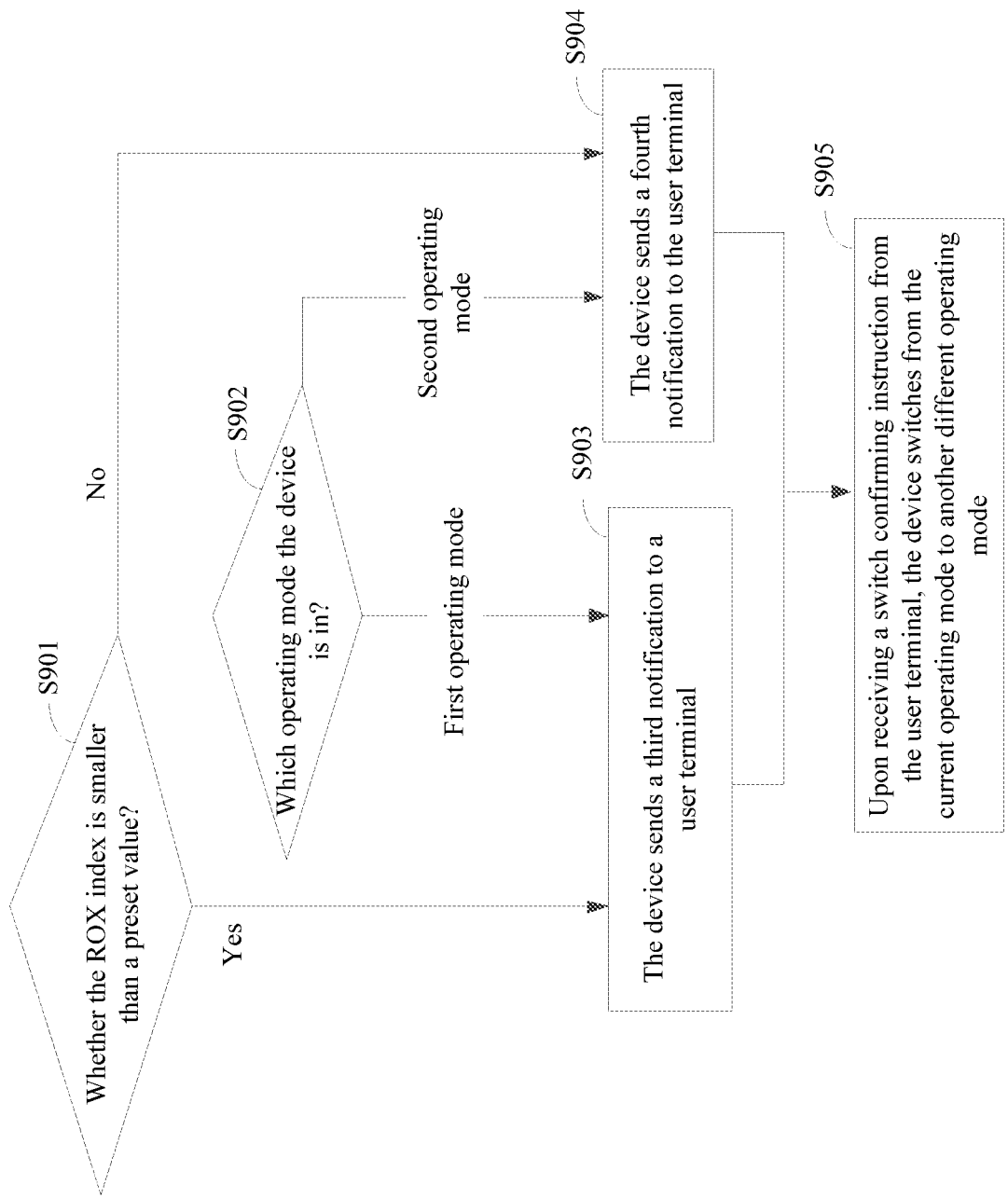
FIG. 9A is a schematic flowchart of a semi-automatic triggering strategy for triggering mode switching of a device for respiratory therapy.

In a possible implementation, as shown in FIG. 9A, which is a schematic flowchart of a semi-automatic triggering strategy for triggering mode switching of a device for respiratory therapy. In step S901, a determination is made whether the ROX index is smaller than the preset value (e.g., 4.88). In step S902, the device can determine the current operating mode in which it is. It should be noted that step S902 can be performed before or after performing step S901, or during the process of performing step S901, which will not be limited by the embodiments of the present disclosure. Based on the determination results of steps S901 and S902, the device can send the third notification or the fourth notification to the user terminal to remind the user via the user terminal that may be necessary to perform the mode switching between the first operating mode and the second operating mode.

Figure 9B:
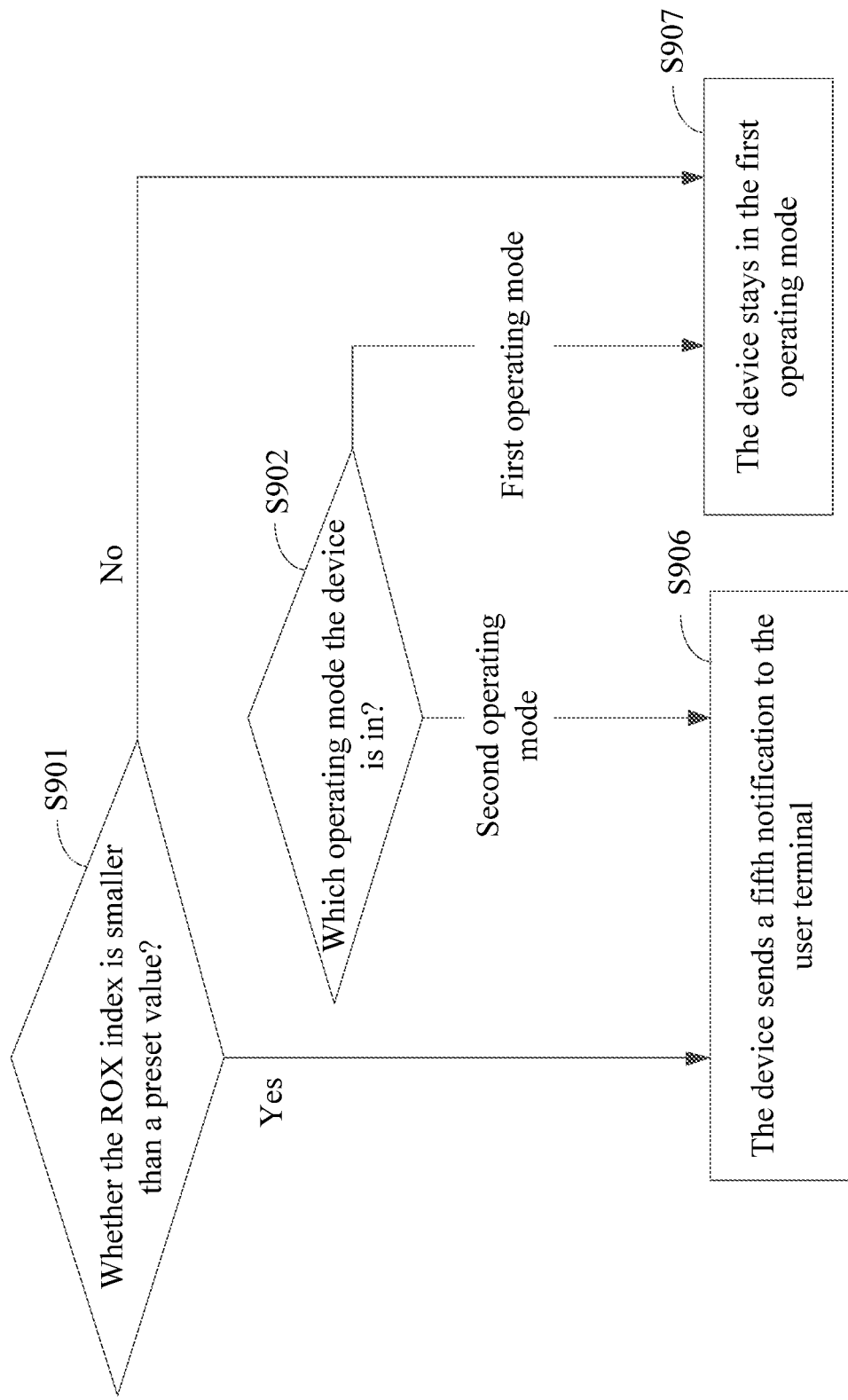
FIG. 9B is a schematic flowchart of another semi-automatic triggering strategy for triggering mode switching of a device for respiratory therapy.

Specifically, upon determining that the ROX index is smaller than the preset value (that is, a patient may be at high risk of HFNC failure) and the device is in the first operating mode (i.e., HFNC mode) currently, the device can send the third notification to the user terminal in step S903 to remind the user via the user terminal that it may be necessary to switch from the first operating mode (HFNC mode) to the second operating mode (NIV mode or INV mode), then the user can confirm whether to conduct the mode switching from the first operating mode to the second operating mode by the user terminal. In a possible scenario, the ROX index is smaller than the preset value but the device is not in the first operating mode, that is, a patient may be at high risk of HFNC failure but the device is in the NIV/INV mode (i.e., second operating mode), under this scenario, there may be a need to switch operating mode. For example, when the ROX index is smaller than the preset value and the device is in the NIV mode, but the physical condition of the patient may be deteriorated and INV support is required; for another example, when the ROX index is smaller than the preset value and the device is in the INV mode, but the physical condition of the patient may be improved and the NIV support is required. Considering these situations, in a possible implementation, the device can send a notification only if the ROX index is smaller than the preset value, where the notification indicates that the ROX index is smaller than the preset value. Accordingly, step S602 of triggering mode switching of the device according to the ROX index and the preset triggering strategy for switching the operating mode of the device may further include step S906 as shown in FIG. 9B, which is a schematic flowchart of another semi-automatic triggering strategy for triggering mode switching of a device for respiratory therapy. When the device determines that the ROX index is smaller than the preset value in step S901 and the device is in the second operation mode S902, the device sends a fifth notification to the user terminal in step S906 to remind the user that the ROX index is smaller than the preset value, so that the user may be reminded to visit the patient to learn the physical condition of the patient, and the user may decide to escalate the treatment from the NIV mode to the INV mode or de-escalate the treatment from the INV mode to the NIV mode.

Specifically, upon determining that the ROX index is not smaller than the preset value and the device is in the second operating mode, the device can send the fourth notification to the user terminal to the user terminal in step S904 to remind the user via the user terminal that it may be necessary to switch from the second operating mode to the first operating mode, then the user can confirm whether to conduct the mode switching from the second operating mode to the first operating mode by the user terminal. In a possible scenario, the ROX index is not smaller than the preset value and the device is not in the second operating mode, that is, the HFNC mode is required and the device is in the HFNC mode currently. Under this scenario, the device does not need to send a notification to the patient. Accordingly, step S602 of triggering mode switching of the device according to the ROX index and the preset triggering strategy for switching the operating mode of the device may further include step S907 as shown in FIG. 8B. When the device determines that the ROX index is not smaller than the preset value in step S901 and the device is in the first operating mode in step S902, the device stays in its current operating mode in step S907, that is, the device stays in the first operating mode.

According to the third notification or the fourth notification, the user can confirm whether to trigger the mode switching between the first operating mode and the second operating mode by sending the switch confirming instruction to the device directly via the input apparatus or the button on the device or via the user terminal, thereby the device switches from the current operating mode to another different operating mode upon receiving the switch confirming instruction from the user terminal.

In a possible implementation, the step of determining an operating mode of the device may be performed after the step of determining whether the ROX index is smaller than the preset value. In this case, a determination is made whether the ROX index is smaller than the preset value, then the current operating mode of the device is determined based on the determination result of whether the ROX index is smaller than the preset value.

In this implementation, when the ROX index is smaller than the preset value, the device continues to determine whether the current operating mode is the first operating mode, and when the current operating mode of the device is in the first operating mode under the scenario where the ROX index is smaller than the preset value, that is, provided that the device determines that the ROX index is smaller than the preset value (that is, a patient that may be at high risk of HFNC failure) and the device is in the first operating mode (i.e., HFNC mode) currently, the device can send the third notification to the user terminal to remind the user via the user terminal that it may be necessary to switch from the first operating mode (HFNC mode) to the second operating mode (NIV mode or INV mode), then the user can confirm whether to conduct the mode switching from the first operating mode to the second operating mode by the user terminal.

When the ROX index is not smaller than the preset value (that is, the ROX index is equal to or greater than the preset value), the device continues to determine whether the current operating mode is in the second operating mode, and when the current operating mode of the device is in the second operating mode under the scenario where the ROX index is not smaller than the preset value, that is, provided that the device determines that the ROX index is not smaller than the preset value (that is, a patient may be not at high risk of HFNC failure) and the device is in the second operating mode (NIV mode or INV mode) currently, the device can send the fourth notification to the user terminal to remind the user via the user terminal that it may be necessary to switch from the second operating mode to the first operating mode, then the user can confirm whether to conduct the mode switching from the second operating mode to the first operating mode by the user terminal.

According to the third notification or the fourth notification, the user can confirm whether to trigger the mode switching between the first operating mode and the second operating mode by sending the switch confirming instruction to the device via the user terminal, thereby the device switches from the current operating mode to another different operating mode upon receiving the switch confirming instruction from the user terminal.

In a possible implementation, when receiving a notification (the third notification or the fourth notification), the user terminal displays the operating mode to switch to with a "confirmation" and a "cancel" button. The user at the user terminal may press the "confirmation" button to cause the user terminal to send a "confirmation" instruction (i.e., the switch confirming instruction) to the device; or, the user may select the "cancel" button to cause the user terminal to send a "cancel" instruction (i.e., a switch cancel instruction indicating that the mode switching of the device is canceled) to the device. In a possible implementation, upon receiving the switch cancel instruction from the user terminal, the device stays in its current operating mode.

In this implementation, it is the device that makes the determination of whether to switch the operating mode, the user simply needs to confirm whether to perform the mode switching, which not only enables the patient to get timely treatment but also reduces the burden on a physician.

In a possible implementation, when the preset triggering strategy is the fully automatic triggering strategy, step S602 of triggering mode switching of the device according to the ROX index and a preset triggering strategy for switching the operating mode of the device may include the following steps:

S1001, the device determines whether the ROX index is smaller than a preset value;
S1002, the device determines an operating mode of the device;
S1003, upon determining that the ROX index is smaller than the preset value and the device is in the first operating mode, the device switches from the first operating mode to the second operating mode; and
S1004, upon determining that the ROX index is not smaller than the preset value and the device is in the second operating mode, the device switches from the second operating mode to the first operating mode.

Figure 10A:
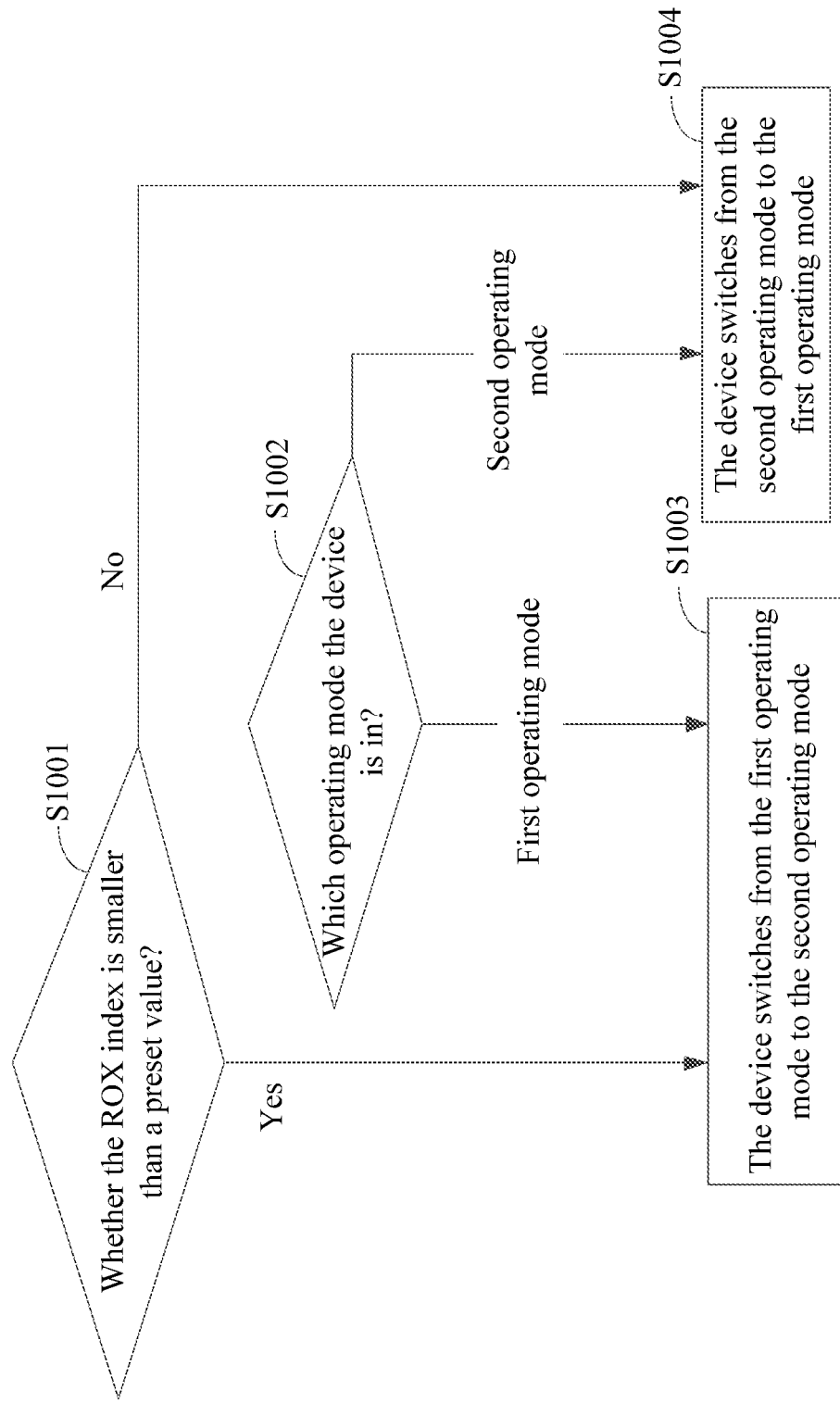
FIG. 10A is a schematic flowchart of a fully automatic triggering strategy for triggering mode switching of a device for respiratory therapy.

In a possible implementation, as shown in FIG. 10A, which is a schematic flowchart of a fully automatic triggering strategy for triggering mode switching of a device for respiratory therapy. Similar to the semi-automatic triggering strategy, in the fully automatic triggering strategy, a determination is made whether the ROX index is smaller than the preset value (e.g., 4.88) in step S1001. In step S1002, the device can determine the current operating mode in which it is. It should be noted that step S1002 can be performed before or after performing step S1001, or during the process of performing step S1001, which will not be limited by the embodiments of the present disclosure.

The Difference between the semi-automatic triggering strategy and the fully automatic triggering strategy is that in the fully automatic triggering strategy, the device automatically triggers the mode switching as required without the confirmation of the user. Based on the determination results of steps S1001 and S1002, the device may trigger the mode switching between the first operating mode and the second operating mode. Specifically, upon determining that the ROX index is smaller than the preset value and the device is in the first operating mode, the device switches from the first operating mode to the second operating mode (step S1003); upon determining that the ROX index is not smaller than the preset value and the device is in the second operating mode, the device switches from the second operating mode to the first operating mode (step S1004).

Figure 10B:
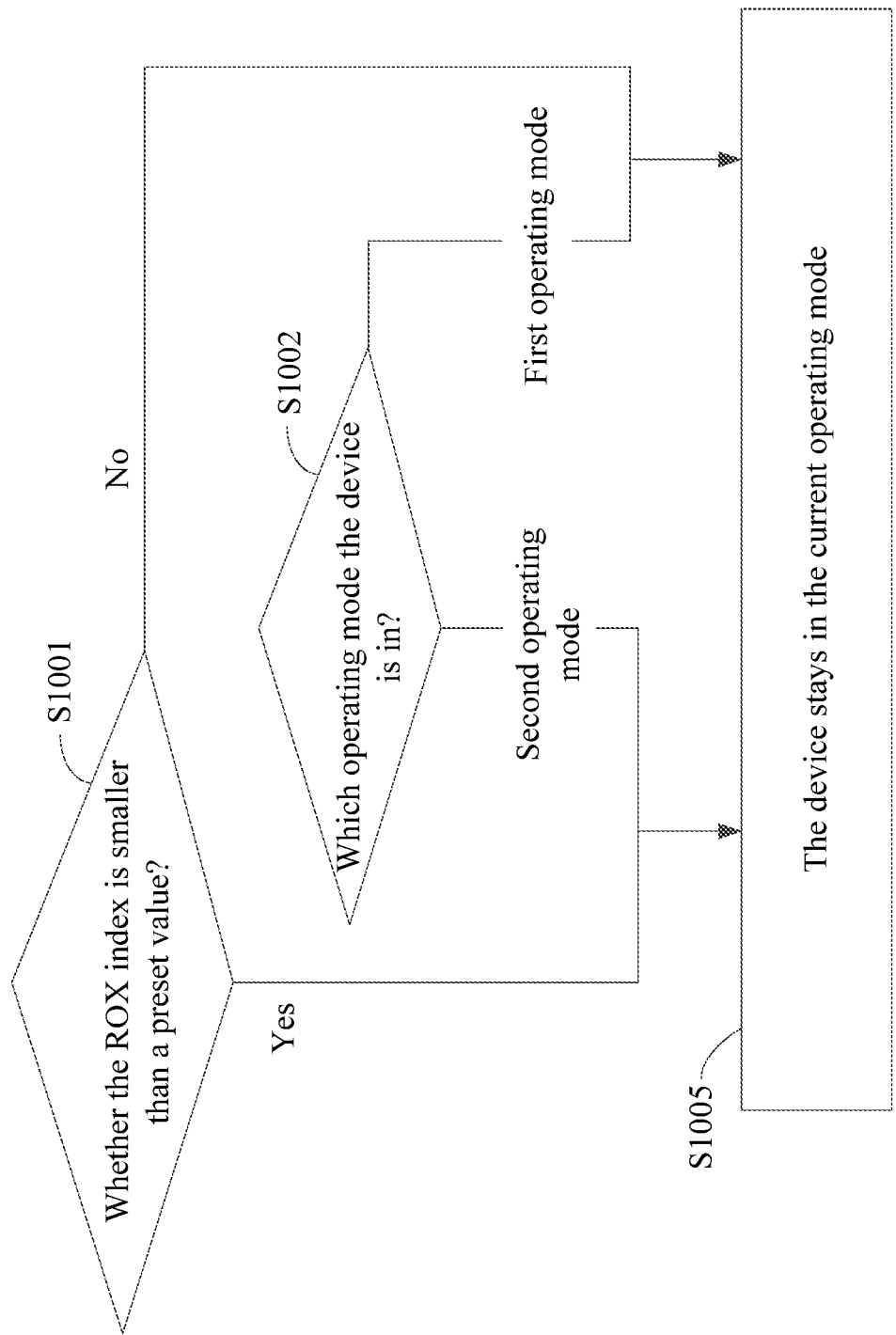
FIG. 10B is a schematic flowchart of another fully automatic triggering strategy for triggering mode switching of a device for respiratory therapy.

By contrast, under the case that the ROX index is smaller than the preset value but the device is not in the first operating mode, or the case that the ROX index is not smaller than the preset value but the device is not in the second operating mode, the device remains in the current operating mode without conducting mode switching. Accordingly, step S602 of triggering mode switching of the device according to the ROX index and the preset triggering strategy for switching the operating mode of the device may include step S1005 as shown in FIG. 10B, which is a schematic flowchart of another fully automatic triggering strategy for triggering mode switching of a device for respiratory therapy. When the device determines that the ROX index is smaller than the preset value in step S1001 but the device is in the second operating mode in step S1002, or when the device determines that the ROX index is not smaller than the preset value in step S1001 and the device is in the first operating mode in step S1002, the device stays in the current operating without conducting mode switching in step S1005.

In this implementation, the operating mode of the device and how to switch the operating mode of the device can be determined by the device itself directly and automatically, and the mode switching can be triggered automatically, so that the user does not need to determine or confirm whether to switch the operating mode and patients can get timely treatment.

With any one of the three preset strategies mentioned above, the device can realize the mode switching between the HFNC mode and the NIV/INV mode.

In a possible implementation, as described for FIG. 2, the device is provided with humidification components configured for humidifying a gas flow delivered to the patient.

In a possible implementation, as described for FIG. 3, the humidification components include a temperature sensor and a heating element connected to the temperature sensor, and the temperature sensor is configured to measure a temperature of the heating element when the device is operating in the first operating mode or the second operating mode.

In a possible implementation, as described for FIG. 4, the device is provided with a flow sensor configured for measuring a flow rate of the gas flow.

In a possible implementation, the humidity of the gas flow is adjustable by the humidification components based on the flow rate, more specifically, the humidity of the gas flow can be adjustable by the humidification components based on the flow rate by the combination of the rough adjustment and fine-tuning described above.

In this embodiment, ROX index, operating mode switching criteria using ROX index, and three different ventilation modes, including HFNC, NIV, and INV, can be implemented in a single integrated device, so as to provide timely proper treatment for patients. In addition, in this embodiment, these three ventilation modes can share the same humidification and heating components and are uniformly controlled by a processor, thereby high-accuracy humidification and temperature control can be achieved for better clinical outcome.

Furthermore, the present disclosure also provides a non-transitory computer-readable storage medium, which stores therein computer-executable instructions which, when being executed by a processor, implement the method for respiratory therapy according to embodiments of the present disclosure.

It should be understood that the processor in the embodiment of the present disclosure may be an integrated circuit chip with a signal processing capability. The above processor can be a general-purpose processor, a Digital Signal Processor (DSP), an Application Specific Integrated Circuit (ASIC), a Field Programmable Gate Array (FPGA) or other programming logic devices, discrete gates, or transistor logic devices, discrete hardware components. The general-purpose processor may be a microprocessor or the processor may also be any conventional processor or the like.

It could be understood that the memory in the embodiment of the present disclosure may be a volatile memory or a non-volatile memory, or may include both volatile and non-volatile memories. The non-volatile memory can be a Read-Only Memory (ROM), a Programmable ROM (PROM), an Erasable PROM (EPROM), and an Electrically EPROM (EEPROM) or flash memory. The volatile memory may be a Random Access Memory (RAM), which is used as an external cache. By way of exemplary but not restrictive description, many forms of RAMs are available, such as Static RAM (SRAM), Dynamic RAM (DRAM), Synchronous DRAM (SDRAM), Double Data Rate SDRAM (DDR SDRAM), Enhanced SDRAM (ESDRAM), Synch Link DRAM (SLDRAM) and Direct Rambus RAM (DR RAM). It should be noted that the memories of the devices and methods described herein are intended to include, but are not limited to, these and any other suitable types of memories.

It should be understood that the above memory is an exemplary but not restrictive description. For example, the memory in the embodiments of the present disclosure may further be a Static RAM (SRAM), a Dynamic RAM (DRAM), a Synchronous DRAM (SDRAM), a Double Data Rate SDRAM (DDR SDRAM), an Enhanced SDRAM (ESDRAM), a Synch Link DRAM (SLDRAM) and a Direct Rambus RAM (DR RAM) and the like. That is to say, the memory in the embodiment of the present disclosure is intended to include but not limited to these and any other suitable types of memory.

The invention claimed is:

1. A device for respiratory therapy, wherein the device is configured with at least two operating modes, and the at least two operating modes comprise a first operating mode for providing high-flow nasal cannula (HFNC) support for a patient and a second operating mode for providing non-invasive ventilation (NIV) support or invasive ventilation (INV) support for the patient;

the device comprises a memory stored with instructions and a processor, the processor is configured to call and run the instructions stored in the memory to execute operations of:

obtaining a Respiratory Rate-Oxygenation (ROX) index based on first parameters; and triggering mode switching of the device according to the ROX index and a preset triggering strategy for switching the operating mode of the device;

wherein the device is provided with humidification components configured for humidifying a gas flow delivered to the patient and a flow sensor configured for measuring a flow rate of the gas flow, the humidification components comprise a temperature sensor and a heating element connected to the temperature sensor, and the temperature sensor is configured to measure a temperature of the heating element when the device is operating in the first operating mode or the second operating mode, and the temperature of the heating element is adjustable based on the flow rate;

wherein the processor is further configured to call and run the instructions stored in the memory to execute operations of:

adjusting the temperature of the heating element to a first temperature value by the following formula:

$$T_{heating\ element}(t) = a_n \cdot Q(t)^n + a_{n-1} \cdot Q(t)^{n-1} + a_{n-2} \cdot Q(t)_{n-2} + \ldots + a_1 \cdot Q(t) + a_0$$

wherein $T_{heating\ element}(t)$ is a temperature of the heating element at time t; $Q(t)$ is a flow rate of the gas flow going through the chamber at time t before heating and humidification; $a_n, a_{n-1}, a_{n-2}, \ldots a_1, a_0$ are coefficients of the formula; and n is a positive integer;

the coefficients of the formula are obtained by fitting experimental data of a series of experiments and are pre-stored in the memory.

2. The device according to claim 1, wherein humidity of the gas flow is adjustable by the humidification components based on the flow rate.

3. The device according to claim 1, wherein the preset triggering strategy is any one of the following: a manual-based triggering strategy, a semi-automatic triggering strategy, or a fully automatic triggering strategy.

4. The device according to claim 3, wherein when the preset triggering strategy is the manual-based triggering strategy, the processor is further configured to call and run the instructions stored in the memory to execute operations of:

determining whether the ROX index is smaller than a preset value;

upon determining that the ROX index is smaller than the preset value, sending a first notification to a user terminal, wherein the first notification indicates that the ROX index is smaller than the preset value;

upon determining that the ROX index is not smaller than the preset value, sending a second notification to the user terminal, wherein the second notification indicates that the ROX index is not smaller than the preset value; and triggering the mode switching of the device based on a switching instruction from a user.

5. The device according to claim 4, wherein,
when the device is in the first operating mode, the switching instruction indicates to switch from the first operating mode to the second operating mode;
when the device is in the second operating mode, the switching instruction indicates to switch from the second operating mode to the first operating mode.

6. The device according to claim 3, wherein when the preset triggering strategy is the semi-automatic triggering strategy, the processor is further configured to call and run the instructions stored in the memory to execute operations of:
determining whether the ROX index is smaller than a preset value;
determining an operating mode of the device;
upon determining that the ROX index is smaller than the preset value and the device is in the first operating mode, sending a third notification to a user terminal, wherein the third notification indicates to switch from the first operating mode to the second operating mode;
upon determining that the ROX index is not smaller than the preset value and the device is in the second operating mode, sending a fourth notification to the user terminal, wherein the fourth notification indicates to switch from the second operating mode to the first operating mode; and
upon receiving a switch confirming instruction from the user terminal, switching the device from the current operating mode to another different operating mode.

7. The device according to claim 3, wherein when the preset triggering strategy is the fully automatic triggering strategy,
the processor is further configured to call and run the instructions stored in the memory to execute operations of:
determining whether the ROX index is smaller than a preset value;
determining an operating mode of the device;
upon determining that the ROX index is smaller than the preset value and the device is in the first operating mode, triggering the device to switch from the first operating mode to the second operating mode; and
upon determining that the ROX index is not smaller than the preset value and the device is in the second operating mode, triggering the device to switch from the second operating mode to the first operating mode.

8. The device according to claim 1, wherein the first parameters are measured by different sensors; the sensors comprise a first sensor configured for measuring oxygen saturation, a second sensor configured for measuring a fraction of inspired oxygen, and a third sensor configured for measuring a respiratory rate; and
the processor is further configured to call and run the instructions stored in the memory to execute operations of:
calculating the ROX index according to the oxygen saturation measured by the first sensor, the fraction of inspired oxygen measured by the second sensor, and the respiratory rate measured by the third sensor.

9. The device according to claim 8, wherein the first sensor is a pulse oximetry, the second sensor is an oxygen concentration sensor, and the third sensor is a flow sensor or a pressure sensor.

10. The device according to claim 8, wherein the sensors are integrated into the device.

11. The device according to claim 8, wherein the sensors are communicatively connected to the device.

12. The device according to claim 1, wherein the processor is further configured to call and run the instructions stored in the memory to execute operations of:
collecting multiple groups of the first parameters measured in a preset time interval;
calculating temporary ROX indexes based on the multiple groups of the first parameters respectively; and
averaging the temporary ROX indexes to obtain the ROX index.

13. The device according to claim 1, wherein the processor is further configured to call and run the instructions stored in the memory to execute operations of:
if a measured temperature value of heated and humidified gas flow has not reached a desired temperature value after adjusting the temperature of the heating element by the formula,
adjusting the temperature of the heating element until the measured temperature value of heated and humidified gas flow reaches the desired temperature value.

14. The device according to claim 1, wherein the processor is further configured to call and run the instructions stored in the memory to execute operations of:
measuring values of the temperature of the heating element at different gas flow rates when a desired temperature value of heated and humidified gas flow is reached;
recording the values of the temperature of the heating element and values of the different gas flow rates; and
obtaining a functional relationship between the temperature of the heating element and the gas flow rate by fitting the recorded values of the temperature of the heating element and the recorded values of the different gas flow rates, to obtain the coefficients of the formula.

15. A method for respiratory therapy applied in a device configured with at least two operating modes, and the at least two operating modes comprise a first operating mode for providing high-flow nasal cannula (HFNC) support for a patient and a second operating mode for providing non-invasive ventilation (NIV) support or invasive ventilation (INV) support for the patient; the method comprising:
obtaining a Respiratory Rate-Oxygenation (ROX) index based on first parameters; and
triggering mode switching of the device according to the ROX index and a preset triggering strategy for switching the operating mode of the device;
wherein the device is provided with humidification components and a flow sensor, the humidification components comprise a temperature sensor and a heating element connected to the temperature sensor, and the method further comprises;
humidifying, by the humidification components, a gas flow delivered to the patient;
measuring, by the flow sensor, a flow rate of the gas flow;
measuring, by the temperature sensor, a temperature of the heating element when the device is operating in the first operating mode or the second operating mode; and
adjusting the temperature of the heating element based on the flow rate;
wherein the method further comprises:
adjusting the temperature of the heating element to a first temperature value by the following formula:

$$T_{heating\ element}(t) = a_n \cdot Q(t)^n + a_{n-1} \cdot Q(t)^{n-1} + a_{n-2} \cdot Q(t)_{n-2} + \ldots + a_1 \cdot Q(t) + a_0$$

wherein $T_{heating\ element}(t)$ is a temperature of the heating element at time t; Q(t) is a flow rate of the gas flow going through the chamber at time t before heating and humidification; $a_n, a_{n-1}, a_{n-2}, \ldots a_1, a_0$ are coefficients of the formula; and n is a positive integer;

the coefficients of the formula are obtained by fitting experimental data of a series of experiments and are pre-stored in the memory.

16. The method according to claim 15, wherein the preset triggering strategy is a manual-based triggering strategy;

wherein the triggering mode switching of the device according to the ROX index and the preset triggering strategy for switching the operating mode of the device comprises:

determining whether the ROX index is smaller than a preset value;

upon determining that the ROX index is smaller than the preset value, sending a first notification to a user terminal, wherein the first notification indicates that the ROX index is smaller than the preset value;

upon determining that the ROX index is not smaller than the preset value, sending a second notification to the user terminal, wherein the second notification indicates that the ROX index is not smaller than the preset value; and triggering the mode switching of the device based on a switching instruction from a user.

17. The method according to claim 16, wherein, when the device is in the first operating mode, the switching instruction indicates to switch from the first operating mode to the second operating mode;

when the device is in the second operating mode, the switching instruction indicates to switch from the second operating mode to the first operating mode.

18. The method according to claim 15, wherein the preset triggering strategy is a semi-automatic triggering strategy;

wherein the triggering mode switching of the device according to the ROX index and the preset triggering strategy for switching the operating mode of the device comprises:

determining whether the ROX index is smaller than a preset value;

determining an operating mode of the device;

upon determining that the ROX index is smaller than the preset value and the device is in the first operating mode, sending a third notification to a user terminal, wherein the third notification indicates to switch from the first operating mode to the second operating mode;

upon determining that the ROX index is not smaller than the preset value and the device is in the second operating mode, sending a fourth notification to the user terminal, wherein the fourth notification indicates to switch from the second operating mode to the first operating mode; and upon receiving a switch confirming instruction from the user terminal, switching the device from the current operating mode to another different operating mode.

19. The method according to claim 15, wherein the preset triggering strategy is a fully automatic triggering strategy;

wherein the triggering mode switching of the device according to the ROX index and the preset triggering strategy for switching the operating mode of the device comprises:

determining whether the ROX index is smaller than a preset value;

determining an operating mode of the device;

upon determining that the ROX index is smaller than the preset value and the device is in the first operating mode, triggering the device to switch from the first operating mode to the second operating mode; and upon determining that the ROX index is not smaller than the preset value and the device is in the second operating mode, triggering the device to switch from the second operating mode to the first operating mode.

20. The method according to claim 15, wherein the obtaining the ROX index based on the first parameters comprises:

collecting multiple groups of the first parameters measured in a preset time interval;

calculating temporary ROX indexes based on the multiple groups of the first parameters respectively; and averaging the temporary ROX indexes to obtain the ROX index.

* * * * *